(12) United States Patent
Van Der Raad-Meijer et al.

(10) Patent No.: US 10,172,682 B2
(45) Date of Patent: Jan. 8, 2019

(54) MEDICAL DEVICE PACKAGING

(71) Applicant: TEVA PHARMACEUTICALS INTERNATIONAL GMBH, Jona (CH)

(72) Inventors: Yvette Jacqueline Van Der Raad-Meijer, Hoofddorp (NL); Johannes Wilhelmus Maria Sanders, Hoofddorp (NL)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 0 days.

(21) Appl. No.: 15/631,002

(22) Filed: Jun. 23, 2017

(65) Prior Publication Data

US 2017/0367780 A1 Dec. 28, 2017

(30) Foreign Application Priority Data

Jun. 24, 2016 (EP) .................................... 16176250

(51) Int. Cl.
*A61M 5/00* (2006.01)
*A61B 50/33* (2016.01)
*B65D 75/36* (2006.01)
*A61B 50/00* (2016.01)
*A61B 50/30* (2016.01)
*A61M 5/178* (2006.01)

(52) U.S. Cl.
CPC .............. *A61B 50/33* (2016.02); *A61M 5/002* (2013.01); *B65D 75/366* (2013.01); *A61B 50/30* (2016.02); *A61B 2050/0065* (2016.02); *A61B 2050/0082* (2016.02); *A61M 5/178* (2013.01); *A61M 2209/06* (2013.01)

(58) Field of Classification Search
USPC .......................... 206/365, 363, 364, 807, 815
See application file for complete search history.

(56) References Cited

U.S. PATENT DOCUMENTS

| 4,753,345 | A | * | 6/1988 | Goodsir | ................ | A61M 5/008 |
| | | | | | | 206/365 |
| 5,156,267 | A | * | 10/1992 | Yates, Jr. | ............ | A61M 5/3205 |
| | | | | | | 206/364 |
| 5,293,993 | A | * | 3/1994 | Yates, Jr. | ............ | A61M 5/3205 |
| | | | | | | 206/365 |
| 2004/0238391 | A1 | * | 12/2004 | Pond | ...................... | A61C 3/005 |
| | | | | | | 206/369 |

(Continued)

*Primary Examiner* — Jacob K Ackun
(74) *Attorney, Agent, or Firm* — David S. Safran; Roberts Mlotkowski Safran Cole & Calderon, P.C.

(57) ABSTRACT

Packaging (4) for an injection device (6, 92), the packaging comprising: a compartment (32) forming a recess configured to house the injection device therein, the compartment extending in a longitudinal direction, a depth direction, and having a variable lateral width to accommodate the injection device; a first sidewall (54) extending in the depth direction and longitudinal direction contiguous a portion of the compartment; and a lip (56) adjoining the sidewall and said portion of the compartment, wherein the first sidewall is arranged within a field of width of the compartment, the lip arranged at a height (h) from a base of said portion of the compartment, such that the lip and first sidewall prevent user gripping of a housed injection device at said portion of the compartment.

13 Claims, 8 Drawing Sheets

(56) References Cited

U.S. PATENT DOCUMENTS

| | | | |
|---|---|---|---|
| 2007/0225654 A1* | 9/2007 | Hess | A61M 5/008 604/187 |
| 2012/0160723 A1* | 6/2012 | Harms | A61M 5/003 206/438 |
| 2014/0078854 A1* | 3/2014 | Head | A61M 5/002 366/111 |
| 2014/0360903 A1* | 12/2014 | Iio | A61M 5/002 206/364 |
| 2015/0129442 A1* | 5/2015 | Head | A61M 5/002 206/366 |
| 2017/0128662 A1* | 5/2017 | Schill | A61M 5/002 |

* cited by examiner

MEDICAL DEVICE PACKAGING

TECHNICAL FIELD

The described embodiments relate generally to medical packaging for housing medical devices, and more specifically to medical tray type packaging for housing medical injection devices, including prefilled syringes.

BACKGROUND

Medical tray type packaging of the type for containing a medical device such as a syringe commonly comprises a thermoformed base formed from a thick plastic sheet. The thick plastic sheet provides protection for fragile devices and comprises recesses for containment of the devices. To close the base a tear away or break through lid may be provided as medical blister type packaging. Alternatively, the lid may comprise a thick plastic sheet corresponding to that of the base thus providing a medical tray or medical clamshell type packaging.

Medical tray type packaging differs from traditional pharmaceutical blister packs for unit-dose packaging of tablets in that, for the aforesaid protection of the device, the base web is not collapsible. The device therefore cannot be pushed-though upon extraction. Consequently the process for extraction of a contained device can be more complex. It may comprise removal/perforation of the lid and a user reaching into part of the recess and gripping the device. The device is typically a force fit or other secure fit within the recess. Thus incorrect removal of the device may cause damage thereto and is of particular concern for fragile devices such as prefilled syringes. Moreover incorrect removal may result in a user gripping the device so as to obscure instructions for use or so as to use the device incorrectly.

In spite of the effort already invested in the development of said packaging further improvements are desirable.

SUMMARY

In a first embodiment, there is provided medical packaging to contain and/or protect a medical device. The packaging in particular is suitable for an injection device, and thus includes suitability for injection training devices with dimensions corresponding to those of the associated injection device. The packaging may comprise a compartment configured to at least partially house the medical device. The compartment may form a recess configured to accommodate the medical device. Housing in respect of the medical device can be defined as a substantial portion, e.g. at least 40 or 50% being contained, i.e. the surface area of the device covered within the compartment. The compartment may extend in a longitudinal direction and a depth direction orthogonal thereto. The compartment may have a variable width to accommodate the device. Width can be defined in respect of a longitudinal axis of the medical device when housed and/or a corresponding longitudinal axis of the compartment. The packaging may comprise a guard portion comprising a first sidewall extending in the depth direction and longitudinal direction contiguous the compartment. The packaging may comprise a lip adjoining the sidewall and the compartment. The first sidewall may be arranged within a field of width of the compartment or more particularly of a housed injection device (since the shape of the compartment substantially conforms to the injection device). That is to say that the first sidewall is arranged at a width that is less than a width of part of a housed injection device. In the instance the medical device is a syringe, the width field can be defined by the flange and/or actuation portion of the plunger rod of the syringe. The lip may be arranged at a height (h) from a base of an adjacent portion of the compartment such that the lip and sidewall prevent user gripping (with opposed digits of a hand of the user) of an adjacent portion of a housed injection device. The lip height is thus distinguishable over a height that acts merely to locate the medical device in the compartment and still enable gripping thereof.

Packaging with a guard portion with such a configuration may increase the flexural rigidity of the packaging, for example, by increased second moment of inertia. It may, in embodiments, be desirable to have a more rigid packaging to prevent a user from extracting the medical device in a less preferable manner, for example, by pressing through the bottom exterior of the compartment to collapse the compartment and eject the medical device therefrom, as would be exemplified by a blister pack configuration.

Packaging with a guard portion with such a configuration may receive the digits of a hand of a user in abutment with the first sidewall, which acts to isolate the digits from being able to grip an adjacent portion of the medical device. In this way a user can be guided to gripping of portions of the medical device which are not guarded by the guard portion. The portions guarded may be those which are vulnerable to handling and/or dangerous to a user if gripped, such as a needle of a syringe.

Packaging with a guard portion with such a configuration may provide the appearance of the medical device as floating or suspended in the packaging.

Corresponding first sidewalls and lips may be arranged on opposed sides of the compartment. That is to say that two first sidewalls may be arranged at the same longitudinal position with the same functional configuration but not necessary with exactly the same dimensions. Packaging with such a configuration may further enhance the effect of a single such arrangement.

The guard portion may comprise a first channel, the channel comprising a base adjoining the first sidewall and a second sidewall. The second sidewall may be arranged at a width that is less than a width field of the compartment, or in particular at a width field that is less than a width of part of a received injection device. Packaging with such a configuration may provide a compact arrangement of the channel, thus enabling more than one compartment with said channel arrangement to be arranged adjacent each other. Corresponding first and second channels may be arranged on opposed sides of the compartment. That is to say that two channels may be arranged at the same longitudinal position with the same functional configuration but not necessary with exactly the same dimensions. Packaging with such a configuration may further enhance the effect of a single channel arrangement.

The channel may be arranged to prevent housing of the medical device therein. Housing in respect of the channel can be defined as for the compartment and can require a substantial portion contained, e.g. at least 40 or 50% of the surface area of the device covered. In particular, the channel may be dimensioned differently to the compartment, such as in width and/or length such that an injection device houseable in the compartment is not houseable in the channel. The compartment may be complementary in shape to that of the medical device for housing therein. The channel may have a profile which is non-complementary to that of the compartment. Therefore, the medical device cannot be housed therein. The channel may have one or more of the following arrangements such that the medical device is not houseable therein: a maximum length in the longitudinal direction of less than the maximum length of the compartment; maximum width between the first sidewall and a second sidewall less than the maximum width of the compartment; a width between the first sidewall and a second sidewall less than the width of an adjacent portion of the compartment; the channel comprising abutment means to block housing of the injection device in the channel. The abutment means may comprise one or more protrusions that may extend from a base and/or sidewall of the channel to abut a medical device when inserted into the channel. The term "less" in respect of the aforementioned length and/or width may refer to a difference of at least 2.5 or 5%. The length of the compartment may be matched to that of the medical device. The width of the compartment may be matched to that of the medical device.

The compartment may have a planform to correspond to a planform of the associated medical device. Planform may be defined as the periphery of the medical device when viewed in a lateral and longitudinal plane. The compartment may be configured to at least partially house therein a medical device in a predetermined (single) orientation with respect to a longitudinal direction of the device and compartment. For example, the device may not be able to be inserted when rotated 180° from said predetermined orientation with respect to the longitudinal axis and/or translated along said axis by a nominal amount, which may include 5% of the longitudinal length of the device. A compartment with this configuration may ensure that the medical device has particular orientation when at least partially housed such that gripping of a particular portion of the medical device is prevented by the guard portion. The compartment may be configured to at least partially house the device therein with a single orientation by the configuration of portions of the compartment arranged to engage and/or block said device to prevent its insertion into the compartment with alternative longitudinal orientations. Said portions may comprise at least one of: the guard portion: a gripping portion; a retaining portion; the compartment profiled to match device, or other portion arranged for said engagement. One advantage is convenient formation of the compartment.

The channel may be configured to receive digits of a hand of user. The channel may be configured to receive a single digit in a lateral direction and multiple adjacent digits in the longitudinal direction. Said configuration may comprise a width of 8-20 or 8-30 mm. The width may be defined as the lateral distance between the first sidewall and a second sidewall, including said distance at the top of said sidewalls. The channel may have a depth in the depth direction of 5-20 mm, the depth may be defined as the distance from a lowest point on the channel section to the top of the first and/or second sidewall. The channel may comprise a base, which may be arranged at a different depth to the depth of the compartment.

In embodiments where the material of the packaging, or a part thereof, is at least partially transparent a user may not be aware of the channel and associated first sidewall and lip, whereby the user is only aware that they cannot effectively grip the medical device at the adjacent region. A user may thereby be guided to grip the medial device at an alternative portion thereof. The compartment may be at least partially formed of a material that is sufficiently rigid to prevent a user in normal from collapsing the compartment to extract the device therefrom. The material may be plastic with a thickness of 0.1-1 mm or 0.4-0.7 mm. Packaging with such a configuration may ensure the user extracts the device in the desired manner.

A base of a channel may form at least part of a foot of the packaging. The foot may be configured for abutting a support surface (e.g. a table) for supporting the packaging. For example, the entire base may form the foot or parts of the base may be arranged at a greater depth thus forming the foot. Packaging with such a configuration may enable convenient combined formation of the supporting feet, which may save material as opposed to having dedicated feet extensions. The feet may be arranged on opposed sides of the compartment. The feet may be arranged in the longitudinal direction proximal a first and second end of the compartment.

The base of the first channel and the base of the second channel may be interconnected by an interconnecting region to form a foot. The bases and interconnecting region may form a continuously planar region, whereby the bases and interconnecting region are not interrupted, including by any ridges or rims. Packaging with such a configuration may provide a substantial and stable foot, which is conveniently formed by part of the channels. The planar region may be arranged at an end of a housed medical device. The planar region may overlap and extend beyond the end of the medal device. Packaging with such a configuration may provide a substantial and stable foot.

The first sidewall may extend between two portions of the compartment that extend outwardly in the lateral direction, e.g. between the width of first and second parts of a received medical device. As an example the medical device may be a syringe and the mentioned parts may comprise a flange and a user actuation portion of the plunger rod. Packaging with such a configuration may provide a compact arrangement of the sidewall.

At least two discrete first side walls may extend along the same side of the compartment. That is to say that a side of the compartment comprise more than one separately formed first sidewall. Packaging with such a configuration may provide guarding of a housed medical device at more than one discrete location. There may in particular be first sidewalls arranged to prevent gripping of first and second ends of a housed medical device. The first side walls that extend along the same side of the compartment may be separated by a part of a housed medical device, e.g. a flange of a syringe.

The term 'contiguous' with respect to the first/second sidewall and the compartment may be defined as the most proximal portion of said sidewall being arranged within a field of less than 2 or 3 mm from the most proximal portion of the compartment. In a like manner said sidewall could be within a field of 2 or 3 mm from the most proximal portion of a housed medical device.

In an embodiment the first sidewall may be arranged at a width that is greater than a width field of the compartment. Such an embodiment may encompass an injection device that is generally long and slender without any substantial laterally extending parts.

The first sidewalls when arranged on opposed sides of the compartment may each comprise an inclined planar portion extending along inclines planes that intersect at an apex, whereby the injection device when housed in the compartment is within the bounds of the inclined planes. Alternatively the first sidewalls when arranged on opposed sides of the compartment may each comprise a curved portion (e.g. and no planar portion) where they adjoin the lip, wherein a tangent to the curved portion where it adjoins the lip extends along inclined planes which intersect at an apex, whereby the injection device when housed in the compartment is within the bounds of the inclined planes. Packaging with such a configuration may provide the function that upon application of an opposed force to the sidewalls by opposed digits of a user, said digits may be guided from an engaged position in contact therewith to a disengaged position removed from contact therewith without contact with a housed device. The device may thereby be prevented from being knocked out of the compartment by the digits of a user. The term "within the bounds" can be taken to mean that the portion of the house medical device contiguous to the first sidewalls does not intersect one or both of the longitudinal planes. The apex can be arranged above the housed injection device, and may be aligned to the longitudinal axis of the device when housed. The first sidewall may be configured to, upon the application of said opposed force, remain substantially rigid. The device may thereby be prevented from being squeezed out of the compartment by displacement of the first sidewalls, rather the applied force is translated into movement of the digits between the engaged and disengaged positions.

The lip may be arranged to prevent the insertion of a digit of a hand of a user into a region between the lip and a housed device. Said insertion may be prevented by arranging the lip to extend with its adjacent most portion proximal, e.g. within 5 mm or less of a housed device. The lip may have a thickness in a lateral direction of 5 mm or less. The lip may comprise an entirely curved profile.

The lip may be arranged with an apex thereof having a height 'h' that extends from a base of an adjacent section of the compartment to least 30, 40 or 50% of a maximum thickness of the cross-section in the depth direction. The maximum height of the lip may be 70%, 100% or more than the maximum thickness of the cross-section in the depth direction.

The packaging may comprise a retaining portion which is configured to retain a housed device in the compartment. The retaining portion may provide a friction fit and/or force fit for said housed device.

The guard portion may be configured to prevent gripping of a housed device other than at a gripping portion. The guard portion may extend around an entire periphery of a housed device other than at the gripping portion, including extension continuously or in several portions discretely. Packaging with such a configuration ensures guarding of portions of the device other than the gripping portion. In such a configuration the guard portion may, in combination with the embodiment that comprises described sidewall and lip arrangement, alternatively comprise a laterally and longitudinally extending wall that adjoins the compartment.

The gripping portion may be configured to enable gripping of a housed device at a first portion of the device. The first portion may be a single portion of the device, which may be located at one position only on the device so that the user can only grip the device one point in one particular manner. The first portion may be continuous and thus not formed of more than not discrete and separate portions. A user may thereby be guided to removing the medical device from the packaging by gripping a particular portion thereof and/or by gripping the medical device with a particular orientation of the digits of their hand and/or by gripping the medical device so as not to obscure a particular part thereof, such as instructions for use and/or by avoiding gripping of a portion of the medical device that could cause harm to the user, such as a drug delivery member of an injection device. The gripping portion may be configured for gripping of the device in a direction generally orthogonal to the longitudinal axis of the device. The gripping portion may be disposed about a first and second side of the device. The gripping portion may be arranged to receive opposed digits of a hand of a user for gripping opposed sides of a housed device or arranged to receive a single digit on one side with the opposed digit to grip a top portion of the device. The gripping portion may be arranged to receive only a single digit of a hand of a user on opposed sides of a housed device. Said arrangement may comprise only a single digit in the longitudinal direction. One advantage is that a user is presented with a single way to grip a housed device. The gripping portion may comprise a cavity having a base, the base extending on opposed sides of a housed device. The cavity may be formed of one or more discrete portions. The gripping portion may comprise a cavity having a base, the cavity configured to extend beneath and to be distal, including separated by a distance of 2-10 mm, an adjacent most surface of a housed device. One advantage of the cavity is to enable a user to securely grip with their finger print portion rather than their tip portion of their digits. The gripping portion may be tapered, the taper tapering inward from proximal a housed device to narrow end or an apex or distal thereto.

The compartment may be arranged as part of a tray portion. The packaging may comprise a lid portion to close the compartment. The lid portion may comprise a recess for receiving the one or more feet for stacking a like packaging thereon. The lid portion may comprise contours shaped to correspond to a peripheral shape of the syringe or another component which the tray portion is configured to house, including one or more needles; vial; vial adapter.

The lid portion and tray portion may be arrangeable in a closed position to close the medical device housing compartment of the tray portion and optional compartments that may house associated components. The lid portion may comprise first and second recesses defining associated first and second protrusions. The protrusions arranged in the closed position may extend on either side of a portion of the compartment, which in an embodiment is the portion of the compartment that houses the flange of a syringe. The one or both protrusions arranged in the closed position may extend in the depth direction into at least one recess of the tray portion. The recess may comprise the recess of the compartment. The recesses of the tray portion may be arranged on opposed sides of a component of a housed medical device i.e. arranged on opposed sides of a portion of the compartment. The first and second recesses of the lid portion may at least partially define a lid gripping portion therebetween. The lid gripping portion may be suitable for gripping by opposed digits of a hand of a user, which are arranged in the first and second recesses, in a manner suitable for moving the lid portion from the closed position to open the compartment.

The medial device may be an injection device, which may include a syringe, an auto-injector or a pen-injector or similar. The syringe may be a prefilled syringe, which may be prefilled with a medicament. With the device as a syringe, the guard portion may be arranged to prevent gripping of the syringe at, at least part of one or more of the following components thereof: plunger rod; flange for finger gripping; protective cap; plunger rod actuation portion; delivery member; the barrel. The medical device may be an injection training device, which has dimensions corresponding to that of the associated injection device.

In a second embodiment, there is provided a method of housing a medical device in packaging. The packaging may be according to the first embodiment. The method may comprise arranging the device in a compartment of the packaging. The method may comprise preventing a user from gripping the device housed in the compartment by means of a first sidewall arranged within a field of width of the compartment and contiguous the compartment. A lip may adjoin the first sidewall and the compartment.

In a third embodiment, there is provided a method of handling packaging. The method may be a method of extracting a medical device housed in a compartment of packaging. The packaging may be according to the first embodiment. The packaging may comprise a medical device housed in a compartment of thereof. The method may comprise arranging digits of a hand of a user in contact with first and sidewalls arranged on opposed sides of the injection device. The first sidewalls contiguous the compartment, each may have a lip adjoining the first sidewalls and the compartment. The method may comprise applying an opposed force with said digits to grip said sidewalls. The method may comprise the sidewalls projecting said digits to a disengaged position removed from contact therewith without contact with the housed injection device.

In a fourth embodiment, there is provided medical packaging to contain and/or protect a medical device. The packaging may be suitable for the medical device by being specifically shaped to fit the device. The packaging may comprise a tray portion comprising a compartment configured to at least partially house the medical device. The compartment may extend in a longitudinal direction and a depth direction orthogonal thereto. The packaging may comprise a lid portion. The lid portion and tray portion may be arrangeable in a closed position to close at least the compartment of the tray portion. The term 'close' may refer to covering of an exposed portion of the medical device when housed in the compartment. The lid portion may comprise first and second recesses defining associated first and second protrusions, which are arranged on the opposed side thereto. The protrusions may be arranged in the closed position to extend on either side of a portion of the compartment. One or both of said protrusions may be arranged, when the tray and lid portion are in the closed position, to extend, including at least partially, into at least one recess of the tray portion. The recesses of the tray portion may be arranged on opposed sides of the compartment and thus a component of a housed medical device. The first and second recesses may at least partially define a lid gripping portion arranged therebetween. The lid gripping portion may be suitable for gripping by opposed digits of a hand of a user arranged in the first and second recesses in a manner suitable for moving the lid portion from the closed position to open the compartment.

At least one of the protrusions may abut, when the tray and lid portion are in the closed position, a housed medical device, e.g. a barrel and/or plunger rod of a syringe. At least one of the protrusions associated with the first/second recesses of the lid portion may extend, with the lid and tray portion in the closed position, into a recess of the tray portion that comprises: the compartment and/or a gripping portion for user gripping of a housed injection device. The protrusions associated with the first/second recesses of the lid portion may be arranged on opposed sides of a component of a housed medical device. In the instance of the medical device being a syringe, the component may be a barrel, plunger rod, flange or other. An adjoining portion of a base and sidewall of the first and/or second recesses may be curved at least along an edge adjacent and/or end portion of the lid gripping portion. One or both of the protrusions associated with the first/second recesses of the lid portion may be tapered to a narrowing section towards their bases. One or both of the recesses in the tray portion for receiving the protrusions of the lid portion may be tapered to a narrowing section towards their bases. The first and second recesses of the lid portions and the protrusion associated with the corresponding recesses of the tray portion may be arranged to receive each other for stacking of like packaging.

The lid gripping portion may be partially defined by an extension extending in an opposed direction to that of the first and/or second recesses. The sidewall of the recess may in addition define the lid gripping portion. The extension and first and second recesses may extend in opposed directions from a closing surface. The sidewall of the recesses and end of the extension may be aligned, such that they are continuous. The lid gripping portion may have a height, from a base of the first and/or second recesses of at least 10 mm. Opposed ends of the lid gripping portion for abutment with said opposed digits of a user may be separated by at least 20 mm.

In a fifth embodiment, there is provided a method of at least partially housing a medical device in packaging. The packaging may be according to the fourth embodiment. The method may comprise arranging the device in a compartment of a tray portion of the packaging. The method may comprise locating a lid portion of the packaging with respect to the tray portion by inserting protrusions, which are associated with recesses that define a gripping portion of the lid portion, into corresponding recesses of the tray portion. The recesses of the tray portion may be arranged on opposed sides of a component of a housed injection device. The method may comprise closing at least the compartment of the tray portion with the lid portion.

In a sixth embodiment, there is provided a method of extracting an injection device from packaging. The packaging may be according to the fourth embodiment. The method may comprise inserting digits of a hand of a user into first and second recesses of a lid portion of the packaging. The recesses of the tray portion may be arranged on opposed sides of a component of a housed medical device. The method may comprise gripping the lid portion via a portion of the lid portion between the first and second recesses to separate the lid portion from the tray portion, the tray portion at least partially housing the device. The method may comprise separating protrusions associated with the first and second recesses on the lid portion from corresponding recesses arranged on the tray portion.

In a seventh embodiment, there is provided use of the packaging of any of the embodiments disclosed herein for containing a medical device.

In an eighth embodiment, there is provided a kit comprising the packaging of the embodiments disclosed herein and a medical device configured to be at least partially housed within the compartment thereof.

In a ninth embodiment, there is provided a pre-packaged medical device packaged in packaging of any of the embodiments disclosed herein.

The preceding summary is provided for purposes of summarizing some embodiments to provide a basic understanding of aspects of the subject matter described herein. Accordingly, the above-described features are merely examples and should not be construed to narrow the scope or spirit of the subject matter described herein in any way. Moreover, the above and/or proceeding embodiments may be combined in any suitable combination to provide further embodiments. Other features, aspects, and advantages of the subject matter described herein will become apparent from the following Detailed Description, Figures, and Claims.

BRIEF DESCRIPTION OF THE FIGURES

Aspects, features and advantages of embodiments of the present disclosure will become apparent from the following description of embodiments in reference to the appended drawings in which like numerals denote like elements.

DETAILED DESCRIPTION OF EMBODIMENTS

Figure 1:
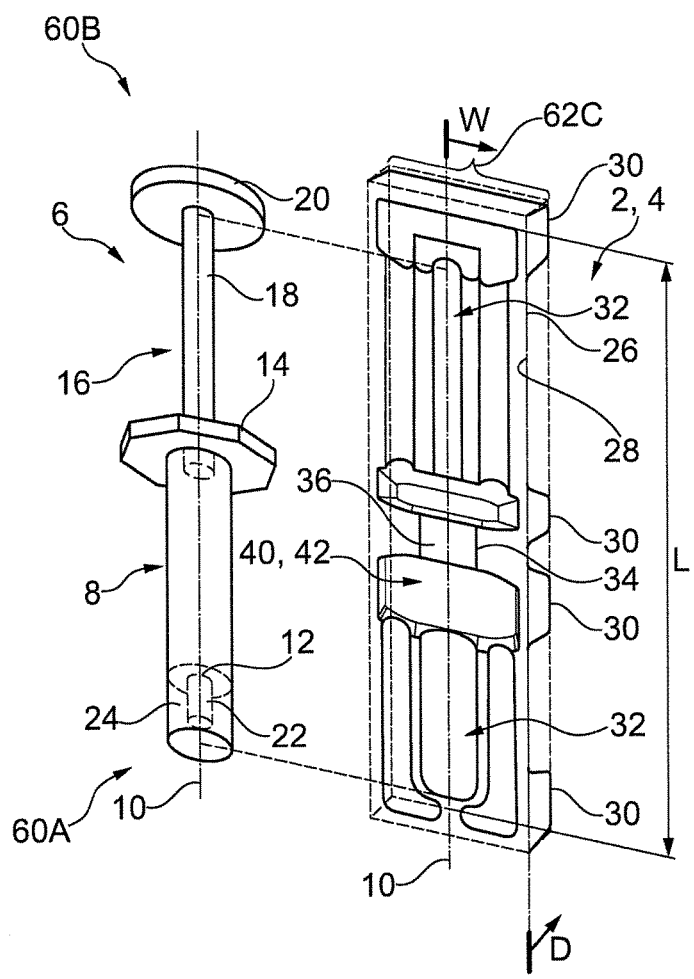
FIG. 1 is an assembly perspective view showing an embodiment packaging and an embodiment injection device.

Before describing several embodiments of the packaging, it is to be understood that the packing is not limited to the details of construction or process steps set forth in the following description. It will be apparent to those skilled in the art having the benefit of the present disclosure that the packaging is capable of other embodiments and of being practiced or being carried out in various ways.

As used herein, the terms "package" or "packaging" includes any material used to wrap or protect a medical device. Packaging can be rigid or flexible. Packaging may include medical packaging, pharmaceutical packaging, and child-resistant packaging. Medical and pharmaceutical packaging can include blister packs, medical clamshell, clamshell trays, and medical trays. The packaging may be sterile or nonsterile. The packaging may include an external carton box.

As used herein, the term "medical device" is an instrument, apparatus or other article, which is intended to be used alone or in combination, specifically for diagnostic and/or therapeutic purposes for human beings. Medical device includes injection devices and in particular syringes, pen injectors, auto-injectors and injection device trainers.

As used herein, the term "grip" means to hold by clasping or grasping with digits of hands of a user with a pincer type action. Grip is in a manner suitable for removing a medical device as defined herein from a compartment as defined herein. Particularly, grip requires a user's opposed digits pressing against the medical device such that frictional forces are greater that the weight of the medical device or the force retaining the medical device in the compartment. The term "digits" refers to one or two fingers acting against an opposed thumb. The fingers are typically selected from the index finger, middle finger, ring finger. The size of user's fingers and thumb are with conventionally accepted ranges. In an example, user fingers and thumbs may be idealised as having a hemispherical tip that extends into a nominal circular cross-sectioned body. For fingers the body may have a diameter that may be 10-20 mm. For thumbs the body may have a diameter that may be 10-30 mm. Further hand dimensions may be as defined by http://usability.gtri.gat-ech.edu/eou_info/hand_anthro.php or similar hand/finger anthropometry study.

As used herein "user" is intended to refer to a medical practitioner, human end user or other human user associated therewith.

As used herein, the term "medicament" includes a substance in liquid or gas form. The medicament may be selected from the group comprising of: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

As used herein, the term "contiguous" means in close proximity without actually touching.

As used herein, the term "compartment" means a portion of the packaging for that provides a containing function in respect of the medical device. In particular the compartment extends around a housed medical device to cover via contact, but may comprise localised contiguous portions between two points of contact, e.g. arising due to manufacturing defects/tolerance allowances/indentations in the device. The compartment may form a recess substantially conforming to the shape of the medical device. In instances wherein the medical device is assembled as a kit, the compartment is defined as housing the main portion of the medical device and not auxiliary parts thereof. An example is a main portion comprising syringe barrel, flange and plunger rod and separate auxiliary parts comprising needles.

As used herein, the term "lip" means a narrow, outwardly projecting edge or rim. In the present disclosure, the term "lip" is a distinct entity and adjoins components, including the compartment and a sidewall. A lip herein can be distinguished from the compartment, which it adjoins, as the lip is entirely contiguous a housed medical device and does not provide a function of covering part of said device. A lip can be distinguished from a sidewall herein, which it adjoins, by a marked changed in gradient of curvature, particularly to a portion that has a greater viable area when viewed in a lateral and longitudinal plane as opposed to a depth and longitudinal plane.

As used herein, the term "channel" means a groove like arrangement with sidewalls adjoined by a base. A base of a channel can herein be distinguished from a sidewall by a portion of the channel that comprises a directional vector of extension with a lateral component greater than a depth component, which includes a flat, laterally aligned base and/or a curved base.

Figure 2:
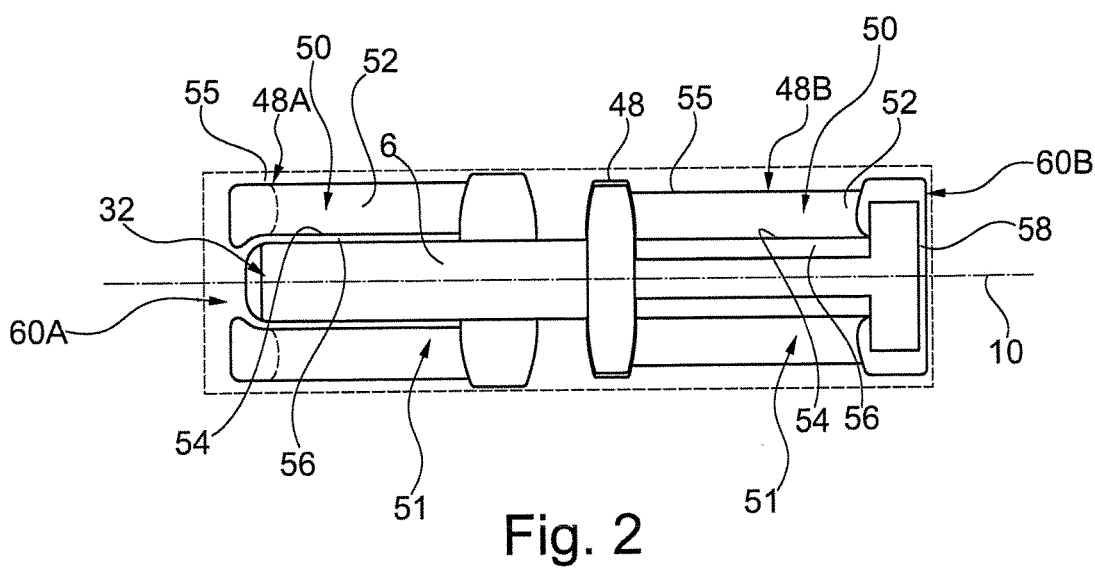
FIG. 2 is an assembly plan view showing the embodiment packaging housing the embodiment injection device of FIG. 2.

Referring to FIGS. 1 and 2, embodiment means for at least partially housing an embodiment medical device is provided. Said means may be in the form of a device housing portion 2 of packaging 4 is shown. The device housing portion 2 may be embodied as part of the packaging 4 in various configurations (as indicated by the dashed line around its periphery). In some embodiments the packaging 4 may comprise other component housing portions, which are in addition to the device housing portion 2 and will be discussed. In some embodiments the packaging 4 may comprise one or more device housing portion 2 (e.g. for housing one or more separate medical devices within the packaging 4). Initially the device housing portion 2 is discussed following by various packaging 4 configurations that it may form part of.

The medical device housed by the device housing portion 2 in the described embodiments comprises an injection device and in particular an embodiment syringe 6. It will be appreciated that the embodiment may be extended to other medical devices as defined herein, in particular to the other herein defined injection devices and associated injection device training devices. Example embodiments for housing other medical devices are discussed subsequent to the syringe embodiment.

Referring to FIG. 1, the syringe 6 may comprises a simple user actuated pump-like device. In an embodiment, the syringe 6 comprises a barrel 8 that may have arranged therein a fluid medicament (or be evacuated by a plunger rod for filling from a vial). The barrel 8 may be elongate along longitudinal axis 10. The barrel may comprise at a distal end thereof an orifice 12 for evacuation of the medicament therefrom. The syringe 6 may comprise at a proximal end of the barrel 8 a flange 14, which may be configured for gripping with one or more digits of a user. The flange 14 may extend laterally from one or both sides of the longitudinal axis 10. The syringe 6 may comprise a plunger rod 16 for user actuation for said evacuation. The plunger rod 16 may be elongate and arranged aligned to the longitudinal axis 10. The plunger rod 16 may comprise at a proximal end thereof a plunger portion 18, which may be fluidically sealed within the barrel 8. The plunger rod 16 may comprise at a distal end a user actuation portion 20. The syringe 6 may comprise a delivery member 22, which is arranged proximal the distal end of the barrel 8, and may be in fluid communication with the orifice 12. The delivery member 22 may comprise one of the following: a hypodermic needle; a nozzle; tubing; other suitable delivery member or attachment for connection to a delivery member (whereby only the former most is illustrated in the figures). The delivery member 22 may be concealed by means of a protective cap 24 or other member (not shown). The plunger rod 16 may be pushed or pulled via the actuation portion 20 and gripping portion 14 to effect the expulsion of fluid or ingress of fluid to the barrel 8 via the orifice 12 and delivery member 22. The syringe 6 may be sterile or unsterile, depending upon the needs of the user. The syringe is formed from materials known to the skilled person. In the barrel may have a diameter of 10-20 mm. In the plunger rod may have a diameter of 8-15 mm. The syringe may have a longitudinal length of 15-20 cm.

In an embodiment device housing portion 2 comprises or forms part of a body of the packaging 4 for housing the medical device. In an embodiment device housing portion 2 may also comprise or form part of a lid portion of the packaging 4 for closing the body. In other embodiments the packaging 4 does not comprise a lid portion. Initially the body will be described and for convenience is referred to hereon as a tray portion 26.

The tray portion 26 may be formed from a single plastic sheet, which is 0.1-1 mm or more preferably 0.4-0.7 mm thick. In an embodiment, the single plastic sheet is a lamination of more than one sheet. The plastic may be a medical grade plastic, such as high-density polyethylene, polyethylene terephthalate (PET). A presently available example is Tyvek® by DuPoint™. In other embodiments the tray portion 26 is formed from other suitable medical grade materials, such as aluminium. The material of the tray portion 26 may be opaque, transparent, or translucent, including coloured tint, such as green, blue etc. The material is typically robust enough to protect the medical device from damage. The material and/or geometric configuration of the tray 26 is typically sufficiently rigid to prevent deformation under compression, buckling, plastic deformation or other loss of conventional form during user extraction of the medical device therefrom. The tray portion 26 may be formed by thermoforming, vacuum forming, casting or other forming process known to the skilled person. Typically the single plastic sheet in planar form is thermoformed to the desired profile via a mould and other associated equipment known to the skilled person.

Figure 4:
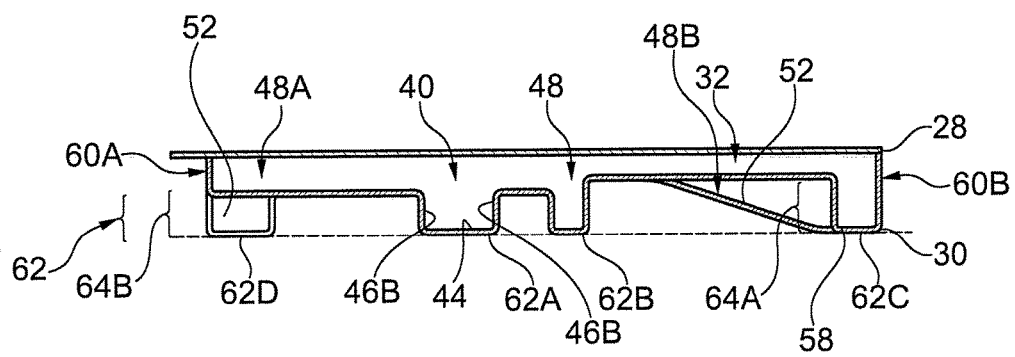
FIG. 4 is a side sectional view taken along line A-A of FIG. 3.

As best viewed in FIG. 4, in an embodiment, the tray portion 26 comprises a first surface 28, which is generally visible to the user when accessing the syringe 6. The tray portion 26 comprises a second surface 30, which may abut a supporting surface, such as a table, when a user accesses the syringe 6. Both surfaces may comprise an interconnected surface or plurality of discrete surfaces, as shown in the embodiment for the first and second surfaces respectively. In embodiments additional intermediate surfaces are provided and will be discussed.

The tray portion 26 comprises a compartment 32, which is configured to at least partially cover a syringe 6 arranged therein, e.g. by at least 40-50% of its surface area. The general profile of the compartment 32 may correspond to that of the syringe 6 as will be discussed. The compartment 32 extends in a depth direction D from the first surface 28 to the second surface 30 or intermediate surfaces. The compartment 32 may have a varying depth generally corresponding to the profile of the thickness in the depth direction of the syringe 6. The compartment has a varying width generally corresponding to the profile of the lateral thickness of the syringe 6. In the embodiment the compartment 32 is elongate in a longitudinal direction with a length L, which corresponds to the axial 10 length of the syringe 6 and has a width W in the lateral direction relative to the axis 10, which corresponds to the lateral thickness of the syringe 6, in particular to accommodate the flange 14 and plunger rod actuation portion 20 thereof.

Figure 5:
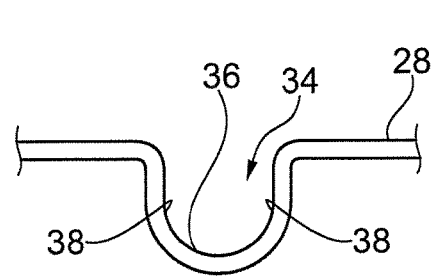
FIG. 5 is a front sectional view taken along line B-B of FIG. 3.
Figure 6:
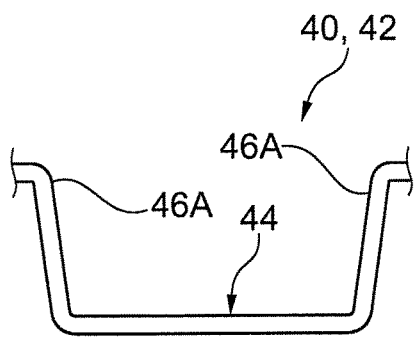
FIG. 6 is a front sectional view taken along line C-C of FIG. 3.

Referring to FIGS. 1 and 5, in an embodiment, the tray portion 26 comprises means for fixedly retaining the syringe 6 therein. Said means may be in the form of a retaining portion 34. The retaining portion 34 is typically part of the compartment 32, but may also be distinct therefrom. In the embodiment the retaining portion 34 is arranged to retain the barrel 8 of the syringe 6. In particular, via abutment with a peripheral surface of the barrel 8, which is proximal the end thereof that has connected thereto the flange 14. The retaining portion 34 comprises a base 36 interconnecting sidewalls 38, which extend along the barrel 8 and engage therewith. The base 36 is profiled to correspond to the profile of the barrel 8, which in the embodiment is circular extending. The sidewalls 38 have an opposed arrangement and extend from the base 36 to the first surface 28. In the illustrated embodiment the sidewalls 38 are generally planar and extend with a substantial component in the depth direction. In particular the sidewalls 38 taper inwardly to the base at approximately 5-30° to the vertical, and have a round with a radius of 2-5 mm applied to a rim adjoining said walls 36 and the first surface 28. The arrangement may facilitate insertion of the syringe 6 into the retaining portion 34. A portion of the sidewalls 28, which is arranged to abut the barrel 8 when abutting the base 36, is arranged an opposed distance which corresponds to the thickness of the barrel 8, in particular, a diameter of the barrel 8. In an embodiment, the opposed distance may be less than the thickness of the barrel, and may be less than said thickness by 2.5-5%, to provide a force fit of the barrel 8. In an embodiment, the opposed distance may be equal to or greater than that of the thickness of the barrel 8, whereby the barrel is not forcibly retained, merely restrained in an off axis 10 direction.

Embodiment variations of the retaining portion that are not illustrated will now be described. In one embodiment the retaining portion 34 may be arranged to retain different portions of the barrel 8 and/or other portions of the syringe 6, including as one or more of the plunger rod 16, flange 14 or protective cap 26. The retaining portion 34 may comprise one or more distinct portions, in an embodiment, two such distinct portions are arranged proximal the distal and proximal ends of the barrel 8. The retaining portion 34 may comprise other arrangements for retaining the syringe 6. In one embodiment it comprise a flat or 'V' shaped base 36 or other suitable configuration. In one embodiment sidewalls 38 may be curved, parallel, 'V' shaped, a combination thereof or other suitably profiled. The retaining portion 34 may have other configurations than force fit. In an embodiment it comprises a friction fit, including by means of ribbing on the sidewalls 38 or via the inclusion of material with higher friction coefficient than the material of the tray portion 26. In an embodiment it comprises a snap fit, including by means of extensions that extend proximal the first surface 28 and from the sidewalls 38 and partially around the syringe 6.

Referring to FIGS. 1-4, 6 and 7, in an embodiment, the tray portion 26 comprises means for enabling gripping, via digits of a hand of a user, of a particular portion syringe 6 arranged in the compartment 32. Said means may be in the form of a gripping portion 40 configured to enable a user to grip, in an oppose manner, part of a particular portion of the syringe 6. In particular, the portion enabled for gripping may be isolated, such that the syringe 6 cannot be gripped elsewhere. In the illustrated embodiment, the portion is the barrel portion 8 of the syringe 6.

In the embodiment gripping portion 40 is arranged to form a cavity 42, which is configured for insertion of the aforedescribed digits of a hand to engage with opposed sides of the barrel 8 arranged in the compartment 32. The cavity 42 extends laterally to the longitudinal axis 10, in the width direction, on both sides thereof. The cavity 42 is configured for insertion of a single digit on either side of the barrel 8 in an opposed manner, whereby the barrel 8 can be gripped by said digits with a pincer type action.

In the embodiment, the cavity 42 comprises a base 44 arranged at the second surface 30. The base may be generally planar as illustrated. The base 44 may have a depth D of 10-20 mm. The base 44 extends both laterally to and aligned to the axis 10. The cavity 42 comprises sidewalls 46 that extend from the base 44 to the first surface 28. The sidewalls 46 comprise axial portions 46A, which extend aligned to the longitudinal axis 10. The sidewalls 46 comprise lateral portions 46B, adjoining the axial portions 46A, which extend generally orthogonally thereto. The axial portions 46A may be 30-50 mm apart. The exact dimension of which will depend of the thickness of the barrel 8 and in addition correspond to conventionally accepted dimensional ranges of user digits. The axial distance of the lateral portions 46B may be 8-15 mm. The axial distance between the lateral portions 46B at the axis 10 may be 20-30 mm and correspond with conventionally accepted dimensional ranges of user digits. The lateral portions 46B may taper inwardly from the longitudinal axis 10 to the adjoining of the axial portions 46A. The taper at the axial portion 46A may be 25-75% of the distance at the axis 10. The axial 46A and lateral portions 46B extend generally linear with an outwardly extending taper from the base 44 to the first surface 28. The taper may be 5-30° to the vertical. A round with a radius of 2-5 mm may be applied to a rim adjoining one or more of the: the sidewalls 46 and the base 44; the sidewalls 46 and the first surface 28; the axial portion 46A and lateral portion 46B of the sidewalls 46. With one or a combination of the aforedescribed configurations the gripping portion 40 is ergonomically shaped to receive a single digit of a user and to permit the aforedescribed pincer movement thereof. The lateral portions 46A may be interrupted by the retailing portion 34, and other associated geometric formations as will be discussed.

Figure 7:
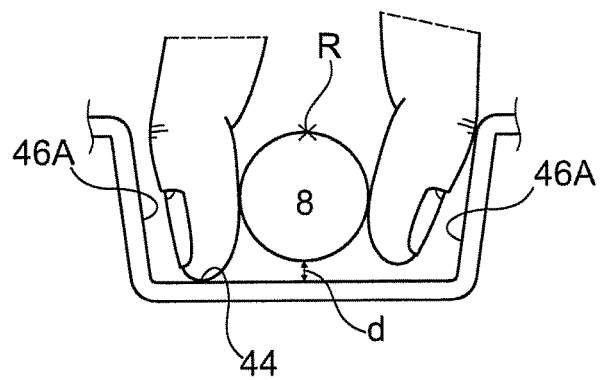
FIG. 7 is a front sectional view taken along line C-C of FIG. 3 showing a user gripping a portion of the syringe.

Referring to FIG. 7, in the embodiment, the base 44 of the cavity 42 is arranged separated from the proximal most periphery of the barrel 8. In particular, the base 44 may be arranged a distance 'd' of 3-6 mm, or other suitable distance, to enable effective gripping of the barrel 8 by the digits of the user. The configuration may enable a finger/thumb print portion of the digit to grip the barrel 8 as opposed to the tip portion. The configuration may enable the digits of a user to grip the barrel 8 with a 'V' arrangement. The configuration may enable the digits of a user to grip an extent of the barrel 8 arranged within the second and third quadrants of the barrel from an angular reference 'R' arranged at the top of the cross-section of the barrel 8. In particular, the portion of the barrel 8 gripped may be at 110-160° anticlockwise and/or clockwise from said reference 'R'.

Embodiment variations of the gripping portion that are not illustrated will now be described. In an embodiment, the gripping portion 40 may be arranged to enable gripping of different portions of the barrel 8 and/or other portions of the syringe 6, including one or more of the plunger rod 16, flange 14 or protective cap 26. In an embodiment, there is more than one gripping portion to enable gripping of the syringe 6 at more than one portion. In an embodiment, there are two such gripping portions arranged for gripping of the barrel 8 at the proximal and distal ends thereof. The gripping portion 40 may comprise other arrangements for said gripping. In an embodiment, the cavity 42 may have other suitable configurations. The cavity 42 may be a through hole thus obviating the base. The base 44 may be arranged at depths other than that of the second surface 30. The base 44 may be concave, convex or other non-planar arrangement. The cavity 42 may comprise two operatively aligned cavities arranged on either side of the barrel 8. The cavity 42 may only extend on a single side of the barrel 8 and be dimensioned such that a user grips the barrel 8 with one digit via the cavity from proximal a bottom of the barrel 8 and another digit from proximal a top of the barrel 8. The cavity may extend in the direction of the longitudinal axis 10 sufficient axial length to accept more than one digit arranged in adjacent in said axial direction. The planform of the cavity may be generally 'C' shaped, rectangular, comprise linear lateral portions 48B with curved adjoining axial portions 46A, or other suitable shape. When tapered, in a similar embodiment to that illustrated, the lateral portions 46B may come together at an apex, rather than at the illustrated axial portions 46A. The sidewalls 46 in their extension between the base 44 and first surface 28 may be curved or be arranged linear and vertically or have other suitable arrangement. In an embodiment, the base of the cavity may abut the barrel 8.

Referring to FIGS. 1-4, 8-10, in an embodiment, the tray portion 26 comprises means for preventing gripping, via digits of a hand of a user, of one or more portions of syringe 6 arranged in the compartment 32. Said means may be in the form of a guard portion 48 configured to prevent said gripping. In the embodiment, the guard portion 48 is arranged to prevent a user from gripping the syringe 6 at one or all portions of the syringe 6 other than via the gripping portion 48.

Figure 3:
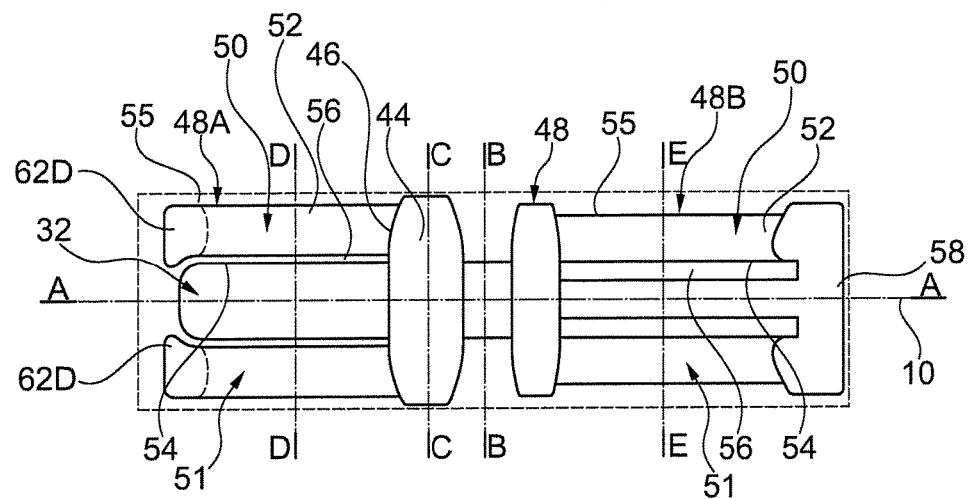
FIG. 3 is a plan view of the packaging of FIG. 1 shown without the embodiment injection device.
Figure 8:
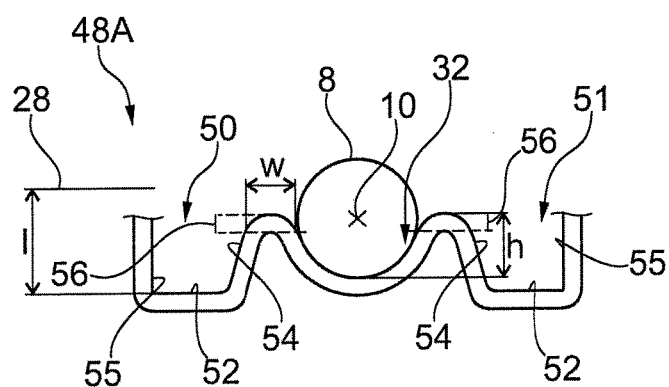
FIG. 8 is a front sectional view taken along line D-D of FIG. 3.

Referring to FIGS. 2, 3 and 8, in an embodiment, the guard portion 48A is arranged proximal a first end portion 60A of the syringe 6. The embodiment guard portion 48A comprises a first sidewall 54, which is arranged contiguous the compartment 32. The first sidewall 54 and compartment 32 are adjoined by a lip 56. In the embodiment the lip 56 comprises an entirely curved profile. The first sidewall 54 is arranged within a field of width (in respect of the axis 10) that is less than a width of one or more parts of the syringe 6 when housed, as can be seen with particular reference to FIG. 2. In the embodiment said part of the syringe 6 is the flange 14 and actuation portion 20 of the plunger rod 18. The first sidewall 54 extends aligned the adjacent portion of the compartment 32, which in the embodiment is the barrel 8.

In the embodiment the first sidewall 54 is formed as part of an optional first channel 50. The channel 50 further comprises a base 52 and second sidewall 55, whereby the base 52 adjoins the first and second sidewalls. The respective first and second sidewall are thus arranged contiguous and further away from the compartment 32. The channel 50 extends aligned the adjacent portion of the compartment 32, which in the embodiment is the barrel 8. In the embodiment, the second sidewall 55 is arranged within a field of width that is less than a width of a part of the syringe 6 when housed, as can be seen with particular reference to FIG. 2. In the embodiment said part of the syringe 6 is the flange 14 only.

In the embodiment, the channel 50 is configured such that the syringe 6 cannot be housed therein. The syringe 6 may in particular not be arrangeable to abut the base 52 of the channel 50. Such a configuration of the channel 50 may be achieved by the channel 50 having: insufficient axial length; and/or lateral width; an arrangement that does not extend coexistent the longitudinal axis 10, e.g. it is offset therefrom, or other suitable arrangement.

The base 52 of the channel 50 may be generally planar and extend aligned to the lateral direction as illustrated. The base 52 may have a maximum depth 'I' of 2-20 mm from the first surface 28. The second sidewall 55 may extend to the first surface 28 allied in the depth direction as illustrated. The first sidewall 56 may, as illustrated, be generally planar and taper from the lip 56 laterally inwardly towards the base 52, including at an angle of 5-30° to the depth direction, to thereby form a narrowing section at the base 52. A round with a radius of 2-5 mm may be applied at an adjoining of one or more of the: the sidewalls 54, 55 with the base 52; the second sidewall 55 and the first surface 28.

The lip 56 may be arranged with an apex thereof aligned with a height 'h', which extends (in the opposed depth direction) from abase of an adjacent cross-section of the barrel 6 to a height, which is 30-70% of a maximum thickness of said cross-section. The lip 56 may comprise a round at its periphery of radii 2-5 mm.

The embodiment guard portion 48A comprises a second channel 51, which as illustrated may have a configuration corresponding to that of the first channel 50, with like reference numerals used to designate like parts. The channels 50, 51 are arranged on opposed sides of the compartment 32.

The associated first sidewalls 54 of the channels 50, 51 are thus arranged on opposed sides of the compartment 32.

The compartment 32 interconnects the first and second channels 50, 51, via the associated lips 56. The compartment 32 may be arranged to extend in abutment with the barrel 8 as illustrated. In particular, it comprises a curved profile to correspond that of the barrel 8. In an embodiment, the compartment 32 may be configured as described for the retaining portion 28.

In the embodiment the compartment 32 and lip 56 can be discriminated by defining the compartment so as to extend around the barrel 8 up to the points where the curvature departs from the barrel 8, as indicated by the dashed line in FIG. 8. In the embodiment the first sidewall 54 and lip 56 can be discriminated by defining the lip 56 to terminate at the same height in the depth direction as the point where curvature departs from the barrel 8, as indicated by the dashed line in FIG. 8. It may also be defied as the portion wherein the curvature substantially changes, with reference to the illustration, at the lip 56 the gradient decreases from a constant at mentioned dashed line. An apex of the lip 56 is arranged at the turning point of its gradient.

Figure 9:
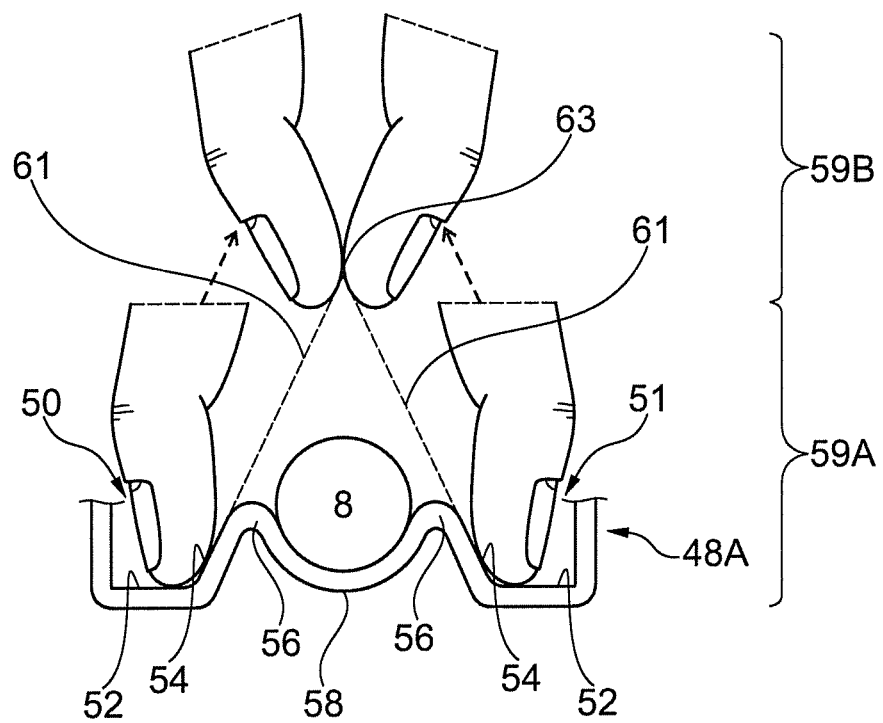
FIG. 9 is a front sectional view taken along line D-D of FIG. 3 showing a user attempting to grip a portion of the syringe.

Referring to FIG. 9, which shows a user attempting to grip the barrel 8 and the blocking effect of the guard portion 48A of FIG. 8. The lips 56 and/or sidewalls 54 acts to shield the barrel 8 from being gripped by opposed digits of a hand of a user. In particular the lips 56 are arranged such that a user cannot insert their digits in a region between the lip 56 and housed syringe 6.

Referring to FIG. 8, in embodiments the lip 56 width 'w' and height 'h' are selected to prevent a user being able to grip the barrel 6 (or in other embodiments, other portions of the syringe/medical device). The width w may be within the range of 1-6 mm, or 1.5-4 mm. As discussed previously, the height h may in the range of 30-70% or 40-60% of the thickness of the medical device. It will be appreciated that the blocking effect of the lip 56 is increased for greater magnitudes of w and/or h, thus in an embodiment a blocking effect may be achieved for a 30% height an 5 mm width, and in an embodiment a blocking effect may be achieved for a 50% height and 2 mm width. A portion of the lip 56 may, as illustrated, be aligned in the lateral direction with the maximum width of the adjacent cross section of the syringe 6.

The sidewalls 54 are sufficiently rigid to prevent a user displacing them to effect pushing out of the barrel 8 from the compartment 32. Moreover, the channels 50, 51 may guide the digits away from gripping the barrel 8 during their insertion into the channel. Particularly, a user is guided to placing the tips of their digits in abutment with the base 52 of the channels 50, where they are blocked by the lip 56. The rounding and/or tapering of the lip 56 and sidewalls 54, including where the sidewall adjoins the base 52, during said insertion can act to guide a digit of a user away from the barrel and into the channel 50.

Referring to FIG. 9, the sidewalls 54, each may comprise a generally planar inclined portion extending along inclined longitudinal planes 61, which come together to form an apex 63. The barrel 8 is arranged within the bounds of the planes 61, i.e. a portion thereof does not intersect one or both of the longitudinal planes 61. The lips 56 and any non-planar portion (not shown) of the sidewalls 54 adjoining the planar portion and lip 56 also arranged within the bounds of the lines. The apex 63 is arranged external the compartment 32 and above the barrel 8. The apex 63 may in particular be aligned to the longitudinal axis. With such a sidewall 54 configuration a user's digits may be guided by the planar portions generally along the lines without contacting the barrel during transition between engaged 59A and disengaged 59B positions. In an alternative embodiment (not shown) the sidewalls each may comprise a curved portion adjoining the lip (and no planar portion at the point of adjoining unlike the previous embodiment), wherein a tangent to the curved portion exactly at the point of adjoining extends along said inclined longitudinal planes, which come together to form at an apex. The inclined longitudinal planes are arranged as per the aforedescribed planar sidewall embodiment. In a further embodiment the latter two embodiments may be combined.

In such embodiments, the depth 52 of the base generally has to be sufficient such that the thumbprint portion of the digit of a user (as opposed to a tip) can abut the sidewall 54 when the tip of the digit abuts the base 52. Typically a depth from the apex of the lip 56 of 5-10 mm is required. Moreover the inclined longitudinal planes may generally be inclined at an angle of 5-30° to the depth direction, as previously discussed. The force to effect transition between the engaged 59A and disengaged 59B positions may be defined as a force which is less than the bucking force of the sidewall 54. In this way fingers of a user may be displaced to the disengaged position before the compartment 32 is deformed to effect squeezing out of the syringe 6 therefrom. The transitioning between said positions may occur in a snapping manner cause by the force applied by the digits overcoming the opposed frictional force. In particular, the aforedescribed curvature and/or tapering of the sidewalls acts as a wedge between the digits, which is forced away from contact therewith.

Figure 10:
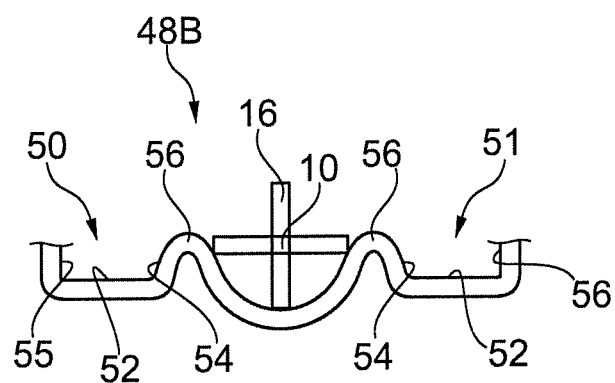
FIG. 10 is a front sectional view through line E-E of FIG. 3.

Referring to FIGS. 2, 3 and 10, an embodiment guard portion 48B is shown, which prevents gripping of the plunger rod 16 of the syringe 6, where like reference numerals designate like components. In this embodiment, the first sidewall 54 extends between the width of first and second parts of a housed syringe, said parts comprising the flange 14 and actuation portion 20 of the plunger rod 16. The lips 56 extend to a greater height h, including 55-70%, to provide greater protection from a user gripping the plunger rod 16. Such an arrangement may be preferable for particular cross-sectional shapes that are more prone to gripping, and example is the X-shaped section of the embodiment plunger rod 16.

The guard portions 48A and 48B both prevent gripping of first 60A and second 60B ends of a housed syringe 6. In combination they provide two discrete first sidewalls 54 that extend along a side of the compartment.

Embodiment variations of the guard portion that are not illustrated will now be described. In one embodiment here may be a single channel 50 arranged adjacent to the syringe 6 with the herein described configuration. In embodiments that comprise two channels the channels may have different configurations independent from each other, e.g. any of the embodiments described herein. In one embodiment the channel may be a through hole thus obviating the base 52. In other embodiments the base of the channel may extend aligned in the longitudinal direction or inclined thereto or with other suitable configuration. The base of the channel may extend aligned in the lateral direction or inclined thereto or with other suitable configuration. The base may have a profile other than planar, including, curved, stepped or other. The base may be arranged at the same depth as the maximum depth of the compartment or at a greater or lower depth. The second sidewall of the channel in the longitudinal direction may have a profile other than planar, including curved, stepped or other. The second sidewall, in the direction extending from the base to the first surface, may have a profile other than planar, including curved, stepped or other. It may also be orthogonal to the first surface or be inclined in either direction with respect to the orthogonal. The first sidewall in the longitudinal direction may have a profile other than planar, including curved, stepped or other. The first sidewall, in the direction extending from the base to the lip, may have a profile other than planar, including curved, stepped or other. It may also be orthogonal to the first surface or be inclined in either direction with respect to the orthogonal. The tapering of the first sidewalls and rounding where they adjoin the base may correspond to the profile of the digits of a user and thus act to isolate movement of the digits when received in the channel.

The lip 56 may have profiles other than round, including an inverted 'V' shape or have a flat top rather than an apex or have the apex of the curve arranged proximal the barrel 6 with lesser curvature distal therefrom. Generally the shape of the lip is selected for roll off of a digit of a user into the channel when abutting the lip vertically. In this way the lip may guide said digit into the channel. A portion of the lip may be arranged within the field of the width of the adjacent section of the housed syringe 6, i.e. arranged underneath the syringe. The guard portion 48 may be arranged to guard other components of the syringe, including one or more of the following components: parts of the barrel 8; the flange 14; the plunger rod 16, including the actuation portion 20; delivery member 22; protective cap 24; other exterior portion of the syringe 6.

In embodiments the guard portion may comprise alternative configurations. In one embodiment the guard portion extends in the lateral and longitudinal plane up to the compartment. An embodiment with such a configuration is shown in FIGS. 1-3 with respect preventing gripping of the flange 14 of the syringe 6.

The embodiment guard portions may be combined. Referring to FIG. 2, the latter described embodiment guard portion guards: the flange 14; a portion of the barrel 8 proximal the flange; the laterally extending ends of the protective cap 24 and plunger rod 14, with the formerly described guard portions 48A, 48B guarding the remaining portion of: the barrel 8; the protective cap 24; the plunger rod 14.

In an embodiment, one or more of the compartment 32, gripping portion 40, guard portion 48 may provide means for abutting the tray 26 on a supporting surface, such as a table (not shown). Referring to FIGS. 1, 2, 4, said means may comprise feet 62. Referring to FIG. 4, in an embodiment the feet 62 comprise a generally planar exterior for said abutment. In the embodiment, the gripping portion 40 and guard portion 48 form the feet 62A-62D. As can be seen in FIG. 4, the base 44 of the cavity 42 of the gripping portion 40 forms a first foot 62A and the base of the cavity of the guard portion associated with the flange 14 forms a second foot 62B.

Referring to FIGS. 3 and 4, the bases 52 of the first channel 50 and the second channel 51 of the guard portion 48B are interconnected by an interconnecting region 58 to form a third foot 62C proximal the second end 60B of the syringe 6. In this embodiment the channels 50, 51 have a bases 52 with varying depth (not shown) such that only a part proximal the second end 60B forms the foot. The bases 52 and interconnecting region 58 form a continuous planar region, that is to say that the foot extends between the bases with a planar surface without interruptions, e.g. due to a ribbing or other like interruption. The interconnecting region 58 overlaps and extends beyond the end of the 60B of the syringe 6.

Referring to FIGS. 3 and 4, the bases 52 of the first channel 50 and the second channel 51 of the guard portion 48A form a foot 62D proximal the first end 60A of the syringe 6. In this embodiment the channels 50, 51 have a bases 52 with varying depth such that only a part proximal the first end 60A forms the foot. In particular, said foot 62D is composed of two discrete portions arranged on opposed sides of the compartment 32.

The tray portion 26 is optionally closed with various configurations, embodiments include a lid portion 66 arranged to form blister packs, medical clamshells, medical trays, and other similar configurations. In an embodiment described in the following the packaging 4 comprises a single device housing portion 2, and thus the lid portion 66 is arranged to close the compartment 32 thereof. It will be appreciated that the embodiment may be adapted to close packaging that comprises more than one device housing portion 2 and/or portions for housing other components, with examples provided later on.

Figure 11:
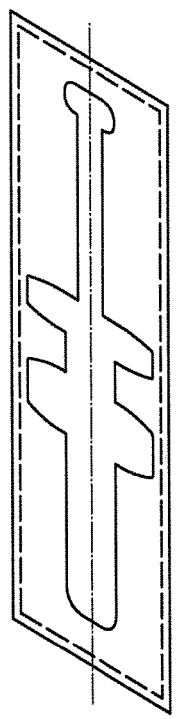
FIG. 11 is an illustrative view showing an embodiment packaging in blister pack configuration.

In an embodiment with a blister pack configuration the compartment 32 of the tray portion 26 may be closed by a lidding film. The lidding film may provide a peel-open feature that can be peeled open using two-hands, including by a knuckle-roll-peel technique. The lidding film can be made from plastic, aluminium, medical grade papers, or other suitable material. The lidding film of the blister pack may be permeable to gas porous to allow sterilization but not permeable to microorganisms. A presently available example plastic material is Tyvek® by DuPoint™. The lidding film may be made from a completely non-permeable or non-breathable film. In instances where a non-breathable film is used, sterilization can be via an electron beam or similar. Referring to FIG. 11, an embodiment packaging 4 with blister pack configuration has the first surface 28 providing planar periphery surrounding the compartment 32. The first surface 28 may be sealed to provide a sealed region comprising the compartment 32. The first surface 28 may receive a lid portion 66 comprising the lidding film to close the compartment 32. The compartment 32 may be sized such that the syringe 6 sits flush or is sunk below the first surface 28. In other embodiments the first surface 28 may have an extension providing a similar such surface for receiving the lidding film.

Figure 12:
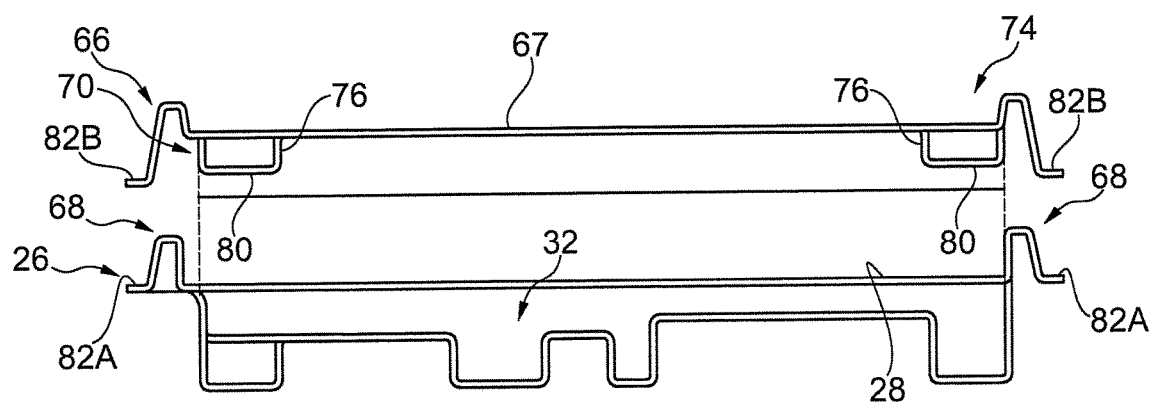
FIG. 12 is an exploded side sectional view showing an embodiment packaging in medical tray configuration.
Figure 13:
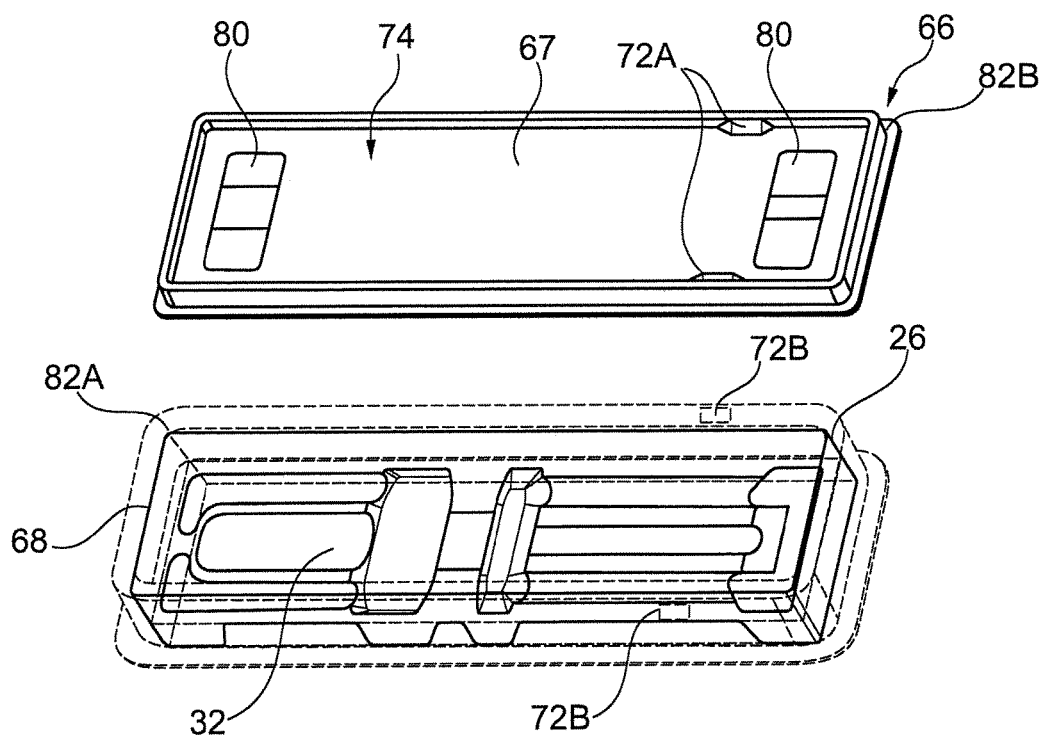
FIG. 13 is a plan view showing the packaging of FIG. 12.

In an embodiment with a medical tray configuration the compartment 32 may be closed by a lid portion 66, which may be fully separable from the tray portion 26. The lid portion may be made from one of the materials previously described for the tray portion. Referring to FIGS. 12 and 13, in an embodiment, the first surface 28 of the tray portion 26 comprises a rim 68 extending around the periphery of the compartment 32 and extending in an opposed depth direction. The lid portion 66 comprises a closing surface 67, which may be generally planar. The closing surface 67 forms a base of a corresponding recess 70 for receiving the rim 68. The rim and recess may have a depth of 5-20 mm.

In the embodiment, the rim 68 and recess 70 comprise retaining portions 72A, 72B to removably attach the lid portion 66 to the tray portion 26. In the embodiment, there are 2 retaining portions. In an embodiment, the retaining portions 72 comprise an extension 72A, which extends outwardly from the recess 70 and a corresponding recess 72B arranged on the rim 68 for receiving the extension 72A. The extensions 72A and recesses 72B are configured for press fit. In an embodiment said press fit is achieved by a wedge shaped extension and corresponding recess for press fitting the wedge, which may include a recess to partially accept the wedge shape.

Referring to FIG. 12, the embodiment the lid portion 66 comprises a further recess 74 arranged opposed the recess 70. The recess 74 may be configured to receive the feet 62 of a tray portion 26 for stacking of another packaging 4 thereon.

In the embodiment, the lid portion 66 comprises extensions 76 to define one or more retaining portions 80 for retaining the syringe 6. The retaining portions 80 may have a configuration as described for the retaining portion 34 of the tray portion. The retaining portions 80 may extend into or abut the compartment 32 for said retention. In the illustrated embodiment there are two retaining portions 80 arranged to retain opposed ends of the syringe 6.

In an embodiment, tray portion 26 comprises a skirt 82A extending around a periphery of the rim 68. The lid portion 66 may comprise a corresponding skirt 82B extending around a periphery of the recess 70. The skirts 82A, 82B configured to abut each other to locate the lid portion 66 on the tray 26.

Embodiment variations of the lid portion 66 that are not illustrated will now be described. In an embodiment retaining portions 72 may have alternative configurations, such as the extension arrange on the rim 68 and the recess arranged on the recess 70. In an embodiment, the retaining portions 72 may be configured for alternative fits, including snap fit, friction fit or other. In an embodiment, the rim 68 and recess 70 may be a force fit, including via tapering of the sidewalls, thus obviating the retaining portions 72. In a configuration not intended for stacking the recess 74 may be obviated. In an embodiment, the lid portion 66 may be hinged at a peripheral edge to provide a medical clamshell configuration. In an embodiment, the first surface 28 and in particular its periphery may be insertable into the recess 74 of the lid portion 66, thus obviating the previously described rim 68. Advantageously, this may ease user access to the medical device in the packaging since no attachment between the lid and the tray needs to be open beforehand.

Figure 14:
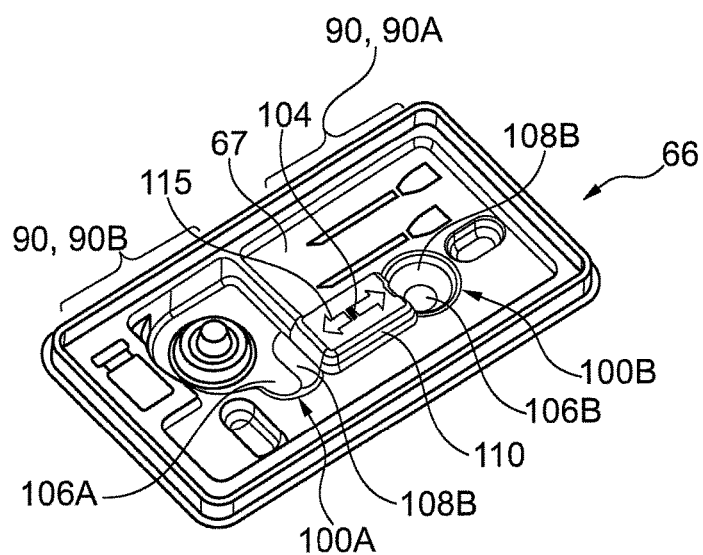
FIG. 14 is a perspective assembly view showing an embodiment packaging in medical tray configuration.
Figure 15:
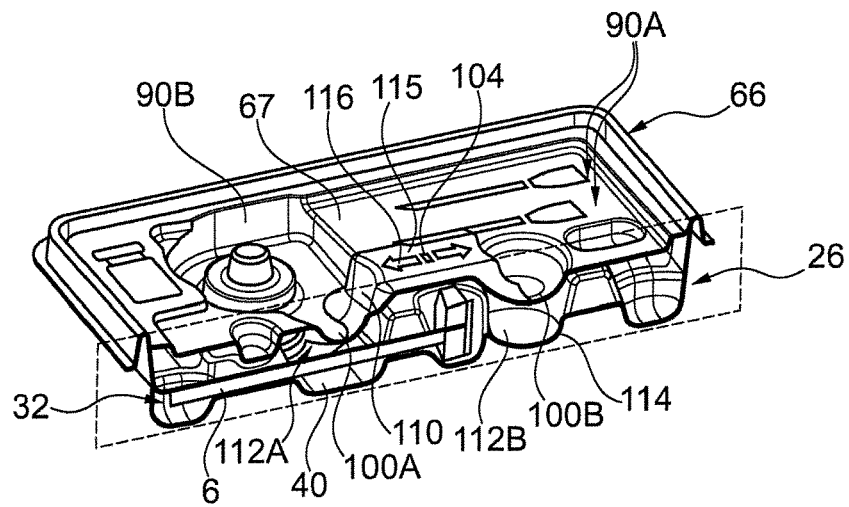
FIG. 15 is a perspective sectional view showing the packaging of FIG. 14.
Figure 16:
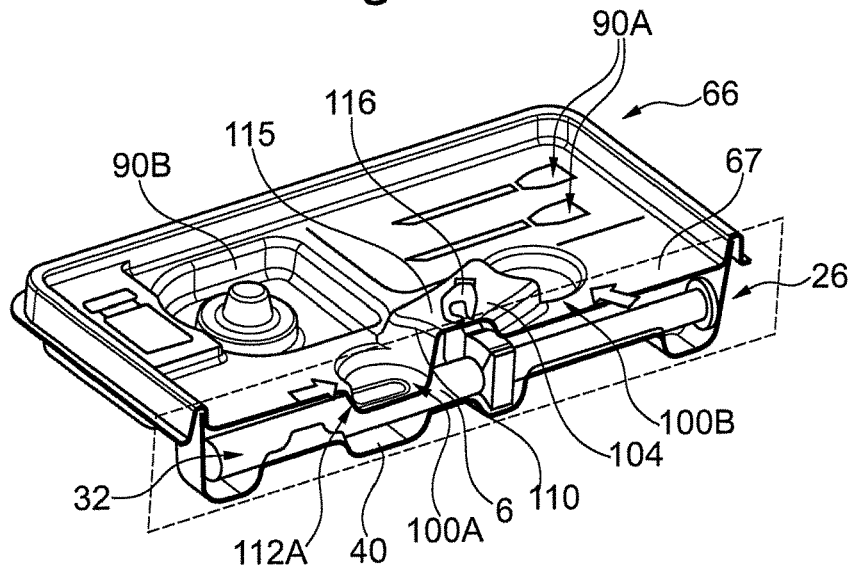
FIG. 16 is a perspective sectional view showing an embodiment packaging in medical tray configuration.

Referring to FIGS. 14-16, in an embodiment the lid portion 66 comprises first 100A and second 100B recesses, which extend generally in the depth direction from the closing surface 67. The recesses define a gripping portion 104 arranged therebetween. The recesses are arranged to receive digits of a hand of a user, typically with one digit per recess, such that the gripping portion 104 can be gripped in an opposed manner for manipulation of the lid portion 66. The lid portion can be mated with a corresponding tray portion 26 in a closed position, as shown in FIGS. 15 and 16, wherein the compartment 32, and other optional component housing portions may be closed by the lid portion 66. The gripping portion 104 can enable manipulation from the closed position to an open position.

The first recess 100A may comprise a base 106A and sidewalls 108A. The first recess 100A may have a depth, measured from the top of the adjacent portion of the gripping portion 104 to the base 106A, sufficient to enable a user to grip the gripping portion securely, which may comprise gripping via a finger/thumb print portion of their digits as opposed to by the tip. This may be achieved by a depth of at least 10 mm or 15 mm. The recess 100A may have a generally circular cross section formed by the sidewalls 108A. The diameter of said section may be at least 20 mm or other suitable dimension to permit the insertion of user's figures/thumbs. The diameter may be 20-30 mm or other suitable dimension to permit the insertion of only a single digit therein. A portion of the sidewall 108A may merge onto other recesses, including those of the identifying contours. The base 106A of the recesses 100A may be curved at least along the edge adjoining the sidewall 108A at least along an edge adjacent most the gripping portion 104. The profile of the curvature can be selected such that, upon the application of an opposed griping force, a figure/thumb print portion of a digit of a user is urged into contacted with the sidewall 108A for enhanced gripping. The radii of curvature may be 1-5 mm. The profile of the curvature may be matched to that of a digit of a user. The sidewall 108A may be generally planar and may taper to a narrowing section at the base 106A outwardly, including at an angle of 5-30° to a plane orthogonal the closing surface 67. The second recess 100B may have a configuration corresponding to that of the first recess 100A, with like reference numerals used to designate like parts.

The gripping portion 104 may include an extension 110, which extends from the closing surface 67 in an opposed depth direction to that of the recesses 100. The distance in the depth direction may be 5-20 mm. The gripping portion 104 of an extension 110 may highlight the portion to be gripped by the user when removing the lid. The sidewalls 108 define first and second ends of the gripping portion 104. Said ends are separated by a suitable distance for stable gripping, which may include 20-60 mm. Said ends can be concave corresponding to the generally circular cross section of the sidewalls 108. The gripping portion 104 may comprise a generally planar top surface 115 between said ends. The sidewalls may adjoin top surface 115 with a round, which can have a radii of 1-5 mm. The top surface 115 may comprise indicia 116 to indicate gripping. Referring to FIG. 15, the indicia 116 can comprise opposed arrows pointing to the first and second ends. Referring to FIG. 16, the indicia 116 can comprise a hand of a user with the digits thereof indicating a pincer gripping action.

The first and second recess 100A, 100B may form corresponding first and second protrusions 112A, 112B on an opposed side of the lid portion 66. The first and second protrusions 112A, 112B may extend at least partially into various recesses of the tray portion 26 said portion and the lid portion 66 are arranged in the closed position. The recesses that the first and second protrusions extend into may comprise the aforedescribed gripping portion 40, compartment 32, or other dedicated recess 114 or a combination thereof. A configuration of interlocking recesses and protrusions can enable more compact packaging and can facilitate more convenient assembly of the lid portion 66 into the closed position. The first and second protrusions 112A, 112B may be arranged, in the closed position, on opposed sides of a component of the syringe 6, such as the barrel 8, plunger rod 16, or other portion. In the illustrated embodiment the component is the flange 14. In this way said component can be accommodated in the gripping portion 104. The gripping portion 104 thus bridges the component. A configuration can enable a more compact packaging.

The first and second protrusions 112A and/or the associated recesses that they extend into on the tray portion 26 may be tapered in the depth direction. The taper may be arranged to provide less tolerance between the protrusions and recesses as the degree of insertion in the depth direction increases, including with a narrowing section towards the base of the recess/protrusions. The taper including the associated sidewalls arranged at an angle of 5-30° to a plane orthogonal the closing surface 67. The protrusions 112A and/or associated recesses 100 may thus have a frustoconical shape. A configuration with such tapering can provide convenient assembly of the lid portion 66 and tray portion 26 since a locating function is provided.

One or both of the protrusions 112 may abut, with the lid portion 66 in the closed position, a portion of the syringe 6 housed in the compartment 32 of the tray portion 26. Referring to FIG. 16, the portion of the syringe abutted is the barrel 6. A base of or each protrusion 112 may abut the syringe 6. The base may be profiled to partially extend around the syringe 6. The lid portion 66 may thereby conveniently locate and secure the syringe 6 in the compartment 32.

Embodiment variations of the lid portion 66 that are not illustrated will now be described. The first and/or second recess may have different configurations to each other, for example, one selected from any of the embodiments described herein. The first and/or second recess may be formed without a base, i.e. a through hole. The first and/or second recess may have a cross section other than circular, including oval, rectangular or other. The sidewall of the recesses may in the depth direction extend in a linear and/or curved manner, it may also be arranged to extend orthogonal of the closing surface. The gripping portion 104 may comprise a top surface which is concave or other. The ends of the gripping surface 104 may be planar or other. The first and/or second recess 112 of the lid portion 66 may be arranged to receive the protrusion associated with the corresponding recess of the tray portion 26. Like packaging with this configuration may be conveniently stacked.

Figure 17:
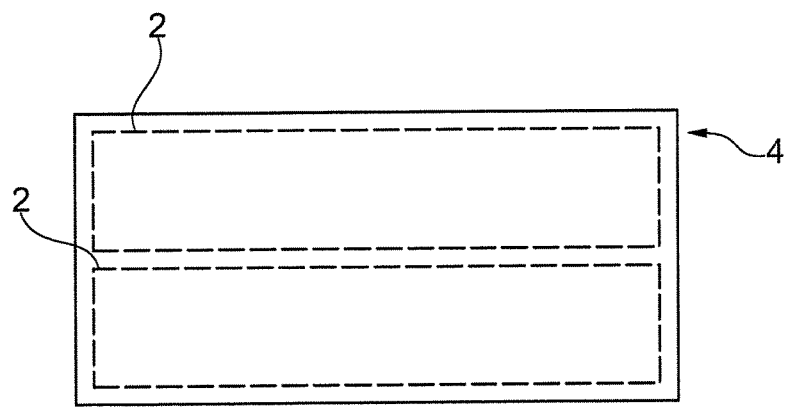
FIG. 17 is an illustrative plan view showing an embodiment packaging.
Figure 18:
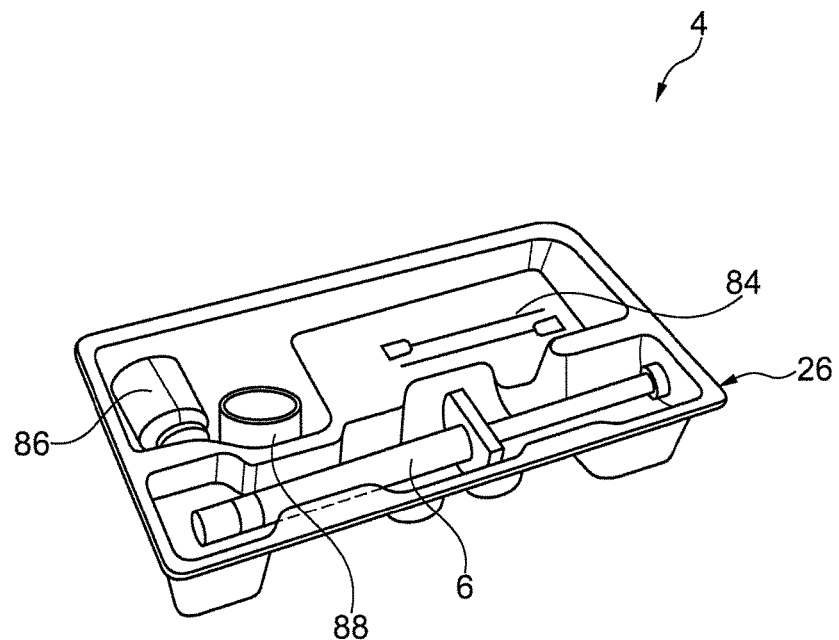
FIG. 18 is a perspective assembly view showing an embodiment packaging housing an embodiment syringe kit.

In embodiments the packaging 4 may comprise more than one device housing portion 2. Referring to FIG. 17 in an embodiment, there are two device housing portions 2. In embodiments the device housing portions 2 are arranged adjacent each other and extend in the same or an opposed direction. The compartments 32 of the one device housing portions 2 may be closed separately or integrally by one or the aforedescribed lid portion 66 arrangements.

In embodiments, the packaging 4 in addition to the device housing portion 2 comprises other component housing portions. The other components may be associated with the device to form a kit or parts thereof. In an embodiment wherein the medical device comprises a syringe 6, the other components may comprise one or more of the following:

one or more needles, including needles which are the same or a different size, and may include needles which are fully exposed or needles that are capped at an end for coupling to a corresponding capped syringe; a vial for or containing the medicament or a component thereof; instructions for use; vial adapter.

Referring to FIGS. 14-16 and 18, an embodiment kit comprise a: syringe 6; needles 84; vial 86, which may contain a medicament; vial adapter 88; instructions for use (IFU). The packaging 4 is generally rectangular in planform. The specific dimensions of the rectangular planform will depend on those of the components arranged therein. In the embodiment the dimensions are 150-200 mm in length, 80-120 mm in width and 10-50 mm in depth. In an embodiment, tray portion 26 comprises a device housing portion 2 that is arranged adjacent to a long edge of said planform. In an embodiment, the opposed long edge comprises in order: the vial 86; vial adapter 88; needles 84. The IFU may be arranged lie in the space between the tray portion 26 and lid portion 66. It will however be understood by that skilled person that the kit within the packaging 4 may have alternative arrangements.

Referring to FIGS. 14-16, in an embodiment, the lid portion 66 comprises identifying contours 90 on the exterior thereof. The identifying contours may comprise recesses and/or protrusions, which correspond to the shape and/or arrangements of one or more of the components arranged on the tray portion 26. The identifying contours 90 may indicate to a user the location and/or orientation of the component. They may be useful for inexperienced users. They may be useful if the component is housed in a sterile packaging that at least partially obscures the component and/or if the packaging itself obscures the components arranged therein. The identifying contours may enhance the flexural rigidity of the lid portion. In an embodiment, the identifying contours 90 are arranged on the lid portion 66 in respect of needles 84 and a vial adapter 88. In respect of the needles 84 the contours 90A are profiled by means of elongate recesses arranged aligned to the needles 84 when housed in the needle housing portion. In an embodiment, the contour 90A may be profiled to indicate an end cap at the end of a needle to further enhance indefinability. In the embodiment there are two needles and thus two recesses. In embodiments there may be other numbers of needles and corresponding numbers of recesses or a different number of contours to the number of needles. In respect of the vial adapter 88 the contours 90B are profiled by means of a circular recess comprising a coaxial frustoconical extension. In other embodiments other suitable arrangement of contours may indicated the vial adapter, including just a circular recess. The recesses/protrusions associated with the identifying contours 90 may abut a portion of the associated component. The component may thus be secured in the tray by the lid portion 66. Moreover the lid portion 66 may be more conveniently located on the tray portion 26 during closing of the packaging 4.

In an embodiment not shown a kit comprises one or more device housing portions 2 for housing a prefilled syringe and one or more needles for use therewith.

Figure 19:
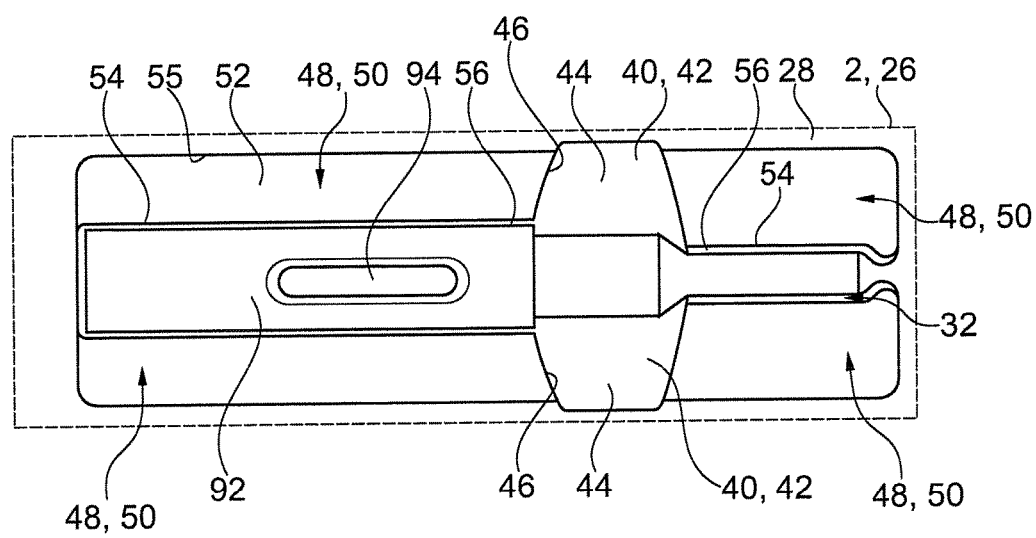
FIG. 19 is a plan view showing an embodiment packaging housing an embodiment auto-injector.

As discussed herein the described embodiments of the device housing portion 2 may be configured to house other medical devices, including the mentioned injection devices. Referring to FIG. 19 in an embodiment, the device housing portion is configured to house an auto-injector 92, where corresponding reference numerals designate corresponding components. In the embodiment, the guard portion 48 acts to prevent a user from gripping the device other than at the gripping portion 40, whereby the gripping portion 40 is arranged such that a user grips a housing 98 of the auto-injector 92 so as to avoid obscuring by gripping the dosage delivery window 94 and instructions for use (not shown) and the ends of said injector. The guard portion 40 comprises the aforedescribed embodiment with a first sidewall 54, base 52 and other associated components, with like reference numerals used to designate like parts. The compartment 32 may be closed by a lid portion (not illustrated) comprising the aforedescribed lid gripping portion.

Embodiment variations of the device housing portion 2 for the auto-injector 92 that are not illustrated will now be described. In embodiments the auto-injector does not comprise a dosage delivery window 94 and/or instructions for use. In an embodiment, the auto-injector may comprise a trigger arranged on the housing to effect dosage delivery. The guard portion may be arranged to prevent gripping of said trigger. The shape of the autoinjector is not limited to the illustrated example. In an embodiment the autoinjector may comprises one or more laterally extending portions, such as a flange for gripping. In such embodiments the first sidewall and optionally the second sidewall of the guard portion can be arranged at a width that is less than a width of part of a received autoinjector. In such an embodiment the first sidewall may extend between the width of first and second parts of a housed autoinjector.

It will be appreciated that the embodiments described herein may be suitably adapted for pen-injectors, which may have similar configurations, together with other medical devices including corresponding auto-injector and pen-injector training devices.

One advantage of the combination of the gripping portion and guard portion described herein is that a user can be directed to extract the medical device from the compartment 32 by gripping a particular portion of the device. In an embodiment where the device is a syringe 6, a user can be directed to grip a less fragile or dangerous part of the syringe, such as the barrel 8 rather than the delivery member 22, protective cap 24, or plunger rod 16. In an embodiment where the device is an auto-injector 92, a user can be directed to grip a less fragile or dangerous part of the auto-injector 92, such as the mid portion rather than the ends. Moreover a user may be directed to extract the device with a particular orientation to a hand of the user. The orientation may be an orientation corresponding or a close approximation to that during use, and an example in an embodiment where the device is a syringe 6 the user may be directed to gripping the syringe at the barrel portion proximal the flange. In the embodiment where the device is an auto-injector 92 the user may be directed to gripping the auto-injector at housing portion distal dosage delivery window. Moreover the user may be directed to grip the device with an orientation such that instructions for use arranged thereon are not obscured/are readable.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an."

The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

Unless otherwise explicitly stated as incompatible, or the physics or otherwise of the embodiments, example or claims prevent such a combination, the features of the foregoing embodiments and examples, and of the following claims may be integrated together in any suitable arrangement, especially ones where there is a beneficial effect in doing so. This is not limited to only any specified benefit, and instead may arise from an "ex post facto" benefit. This is to say that the combination of features is not limited by the described forms, particularly the form (e.g. numbering) of the example(s), embodiment(s), or dependency of the claim(s). Moreover, this also applies to the phrase "in one embodiment", "according to an embodiment" and the like, which are merely a stylistic form of wording and are not to be construed as limiting the following features to a separate embodiment to all other instances of the same or similar wording. This is to say, a reference to 'an', 'one' or 'some' embodiment(s) may be a reference to any one or more, and/or all embodiments, or combination(s) thereof, disclosed. Also, similarly, the reference to "the" embodiment may not be limited to the immediately preceding embodiment.

Unless otherwise stated, an object which is said to extend in a particular direction is to be construed as having a component of a directional vector that extends in said direction and does on preclude the extension in alternative directions.

The foregoing description of one or more implementations provides illustration and description, but is not intended to be exhaustive or to limit the scope of the invention to the precise form disclosed. Modifications and variations are possible in light of the above teachings or may be acquired from practice of various implementations of the present disclosure.

LIST OF REFERENCES

4 Packaging
6 Syringe
8 Barrel
10 Axis
12 Orifice
14 Flange
16 Plunger rod
18 Plunger portion
20 Actuation portion
22 delivery member
24 Protective cap
60A, 60B Ends
2 Device housing portion
26 Tray portion
28 First surface
30 second surface
32 Compartment
34 Retaining portion
36 Base
38 Sidewalls
40 Gripping portion
42 Cavity
44 Base
46 Sidewalls
48 Guard portion
50, 51 Channel
52 Base
54 First sidewall
55 Second sidewall
56 Lip
62 Feet
64 Extensions
58 Interconnecting portion
68 Rim
66 Lid portion
67 Closing surface
70 Recess
72 Retaining portion
74 Recess
76 Extensions
80 Retaining portion
82 Skirt
90 Identifying contours
100 Recesses
106 Base
108 Sidewall
112 Protrusions
104 Gripping portion
110 Extension
115 Top surface
116 Indicia
84 Needles
86 Vial
88 Vial adapter
92 Auto-injector
96 Housing
94 Dosage delivery window

The invention claimed is:

1. A combination comprising a packaging and an injection device (6, 92), the packaging comprising:
a compartment (32) forming a recess configured to house the injection device therein, the compartment extending in a longitudinal direction, a depth direction, and having a variable lateral width to accommodate the injection device;
a first sidewall (54) extending in the depth direction and longitudinal direction contiguous a portion of the compartment;
a lip (56) adjoining the first sidewall and said portion of the compartment; and
a first channel (50) comprising a base (52) adjoining the first sidewall (54) and a second sidewall (55),
wherein the first and second sidewalls are arranged within a field of the lateral width of the compartment,
wherein the injection device has an axial length extending along a longitudinal axis and comprises a component having a lateral thickness extending in a lateral direction relative to the longitudinal axis, and
wherein the lip is arranged at a height (h) from a base of said portion of the compartment, wherein the height (h) is in the range of from 30% to 70% of the lateral thickness of said component of the injection device such that the lip and first sidewall prevent a user from gripping said component of the injection device at said portion of the compartment when the injection device is housed in the compartment, the axial length of the injection device extending along the longitudinal direction of the compartment and the lateral thickness of the component extending in the depth direction of the compartment when the injection device is housed in the compartment.

2. The combination of claim 1, wherein a corresponding first sidewall and lip are arranged on an opposed side of the compartment.

3. The combination of claim 1, wherein corresponding first (50) and second (51) channels are arranged on opposed sides of the compartment.

4. The combination of claim 1, wherein the base (52) of a channel (50, 51) forms at least part of a foot (62) for abutting a support surface for supporting the packaging.

5. The combination of claim 1, wherein the base of the first channel and the base of the second channel are interconnected by an interconnecting region (58) to form a foot (62),
wherein said bases and interconnecting region form a continuously planar region, the planar region overlapping and extending from an end of a housed injection device.

6. The combination of claim 1, wherein the first sidewall extends in the longitudinal direction between two laterally extending portions of the compartment.

7. The combination of claim 1, wherein at least two discrete first side walls extend contiguous a side of the compartment.

8. The combination of claim 7, wherein first sidewalls are arranged to prevent gripping of first (60A) and second ends (60B) of a housed injection device.

9. The combination of claim 2, wherein the first sidewalls each comprise an inclined planar portion extending along inclined planes (61) that intersect at an apex (63), whereby the injection device when housed in the compartment is within the bounds of the inclined planes (61).

10. The combination of claim 1, wherein the height (h) of the lip is in the range of from 40% to 60% of the first lateral thickness of said component of the injection device.

11. The combination of claim 1, wherein the component of the injection device is part of a barrel (8), a flange (14), a plunger rod (16), an actuation portion (20), a delivery member (22) or a protective cap (24).

12. A combination comprising a packaging and an injection device, the packaging comprising:
a compartment (32) forming a recess configured to house the injection device therein, the compartment extending in a longitudinal direction, a depth direction, and having a variable lateral width to accommodate the injection device;
a first sidewall (54) extending in the depth direction and longitudinal direction contiguous a portion of the compartment;
a lip (56) adjoining the first sidewall and said portion of the compartment; and
a first channel (50) comprising a base (52) adjoining the first sidewall (54) and a second sidewall (55),
wherein the first and second sidewalls are arranged within a field of the lateral width of the compartment,
wherein the lip is arranged at a height (h) from a base of said portion of the compartment, such that the lip and first sidewall prevent a user from gripping a component of the injection device at said portion of the compartment,
wherein the compartment is arranged as part of a tray portion (26), the packaging comprising a lid portion (66) to close the compartment in a closed position, the lid portion comprising first (100A) and second recesses (100B) defining associated first and second protrusions, the protrusions being arranged in the closed position to extend on either side of a portion of the compartment, and
the first and second recesses of the lid portion defining a lid gripping portion therebetween for user gripping of the lid.

13. The combination of claim 12, wherein the component of the injection device is part of a barrel (8), a flange (14), a plunger rod (16), an actuation portion (20), a delivery member (22) or a protective cap (24).

* * * * *